(12) United States Patent
Russ et al.

(10) Patent No.: US 11,738,012 B2
(45) Date of Patent: *Aug. 29, 2023

(54) TREATMENT OF NEURODEGENERATIVE EYE DISEASE USING PRIDOPIDINE

(71) Applicant: PRILENIA NEUROTHERAPEUTICS LTD., Yakum (IL)

(72) Inventors: Hermann Kurt Russ, Altendorf (CH); Michal Geva, Even-yehuda (IL); Ralph Laufer, Tel Aviv (IL); Aric Orbach, Rehovot (IL)

(73) Assignee: PRILENIA NEUROTHERAPEUTICS LTD., Yakum (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/078,929

(22) PCT Filed: Feb. 24, 2017

(86) PCT No.: PCT/US2017/019266
§ 371 (c)(1),
(2) Date: Aug. 22, 2018

(87) PCT Pub. No.: WO2017/147366
PCT Pub. Date: Aug. 31, 2017

(65) Prior Publication Data
US 2019/0046516 A1    Feb. 14, 2019

Related U.S. Application Data

(60) Provisional application No. 62/299,290, filed on Feb. 24, 2016.

(51) Int. Cl.
*A61K 31/451* (2006.01)
*A61K 45/06* (2006.01)
*A61P 27/02* (2006.01)
*A61P 27/06* (2006.01)

(52) U.S. Cl.
CPC ............ *A61K 31/451* (2013.01); *A61K 45/06* (2013.01); *A61P 27/02* (2018.01); *A61P 27/06* (2018.01)

(58) Field of Classification Search
CPC ....... A61K 31/451; A61K 45/06; A61P 27/06; A61P 27/02–14
See application file for complete search history.

(56) References Cited

U.S. PATENT DOCUMENTS

| | | |
|---|---|---|
| 7,417,043 B2 | 8/2008 | Svan |
| 7,923,459 B2 | 4/2011 | Gauthier et al. |
| 9,006,445 B2 | 4/2015 | Sonesson et al. |
| 9,012,476 B2 | 4/2015 | Zimmermann et al. |
| 9,139,525 B2 | 9/2015 | Wikstroem |
| RE46,117 E | 8/2016 | Sonesson et al. |
| 9,796,673 B2 | 10/2017 | Wu et al. |
| 9,814,706 B2 | 11/2017 | Zimmermann et al. |
| 10,047,049 B2 | 8/2018 | Barel et al. |
| 10,130,621 B2 | 11/2018 | Schmidt et al. |
| 10,322,119 B2 | 6/2019 | Bassan et al. |
| 10,406,145 B2 | 9/2019 | Schmidt et al. |
| 10,603,311 B2 | 3/2020 | Geva et al. |
| 2003/0139423 A1 | 7/2003 | Sonesson et al. |
| 2003/0149294 A1* | 8/2003 | Gutman ............... C07C 405/00 560/55 |
| 2009/0062400 A1 | 3/2009 | Oron et al. |
| 2010/0316731 A1 | 12/2010 | Weinstock et al. |
| 2011/0206782 A1 | 8/2011 | Zhang |
| 2013/0150406 A1 | 6/2013 | Zimmermann et al. |
| 2013/0197031 A1 | 8/2013 | Sonesson |
| 2013/0267552 A1 | 10/2013 | Waters et al. |
| 2014/0088145 A1 | 3/2014 | Hayden et al. |
| 2015/0202302 A1 | 7/2015 | Licht et al. |
| 2016/0095847 A1 | 4/2016 | Sonesson et al. |
| 2016/0166559 A1 | 6/2016 | Sonesson et al. |
| 2016/0243098 A1* | 8/2016 | Geva .................. A61K 31/451 |
| 2017/0020854 A1 | 1/2017 | Licht et al. |
| 2017/0266170 A1 | 9/2017 | Waters et al. |
| 2018/0235950 A1 | 8/2018 | Sonesson et al. |
| 2019/0015401 A1 | 1/2019 | Sonesson |
| 2019/0209542 A1 | 7/2019 | Licht et al. |
| 2019/0350915 A1 | 11/2019 | Bassan et al. |
| 2020/0000785 A1 | 1/2020 | Waters et al. |
| 2020/0030308 A1 | 1/2020 | Schmidt et al. |
| 2020/0092813 A1 | 3/2020 | Kim et al. |

FOREIGN PATENT DOCUMENTS

| | | | |
|---|---|---|---|
| WO | WO 2001/046145 | 6/2001 | |
| WO | WO/2004/103263 | 12/2004 | |
| WO | WO 2004/103263 A2 | 12/2004 | |
| WO | WO 2005/121092 | 12/2005 | |
| WO | WO 2006/040155 | 4/2006 | |
| WO | WO 2008/127188 | 10/2008 | |
| WO | WO-2011107583 A1 * | 9/2011 | ........... A61K 31/451 |
| WO | WO 2012/028635 | 3/2012 | |
| WO | WO 2013/034622 | 3/2013 | |
| WO | WO 2013/086425 | 6/2013 | |
| WO | WO 2013/152105 | 10/2013 | |
| WO | WO 2014/205229 | 12/2014 | |
| WO | WO 2015/112601 | 7/2015 | |
| WO | WO 2016/003919 | 1/2016 | |
| WO | WO 2016/138130 | 9/2016 | |
| WO | WO 2016/138135 | 9/2016 | |
| WO | WO 2017/015609 | 1/2017 | |
| WO | WO 2017/015615 | 1/2017 | |

OTHER PUBLICATIONS

Sahlholm et al. (Psychopharmacology, 2015, 232, 3443-3453) (Year: 2015).*
Mueller (Neuroprotective Properties of Sigma-1 Receptor in Glaucoma, May 1, 2014, https://digitalcommons.hsc.unt.edu/cgi/viewcontent.cgi?article=1758&context=theses) (Year: 2014).*
Sahlholm et al. (Psychopharmacology, 2015, 232, 3443-3453; Other Document 14 of the IDS of Aug. 22, 2018) (Year: 2015).*

(Continued)

*Primary Examiner* — Theodore R. Howell
(74) *Attorney, Agent, or Firm* — Mark S. Cohen; PEARL COHEN ZEDEK LATZER BARATZ LLP (57) ABSTRACT

The subject invention provides a method of treating a subject afflicted with a neurodegenerative eye disease comprising administering to the subject an amount of pridopidine effective to treat the subject.

42 Claims, 4 Drawing Sheets

(56) References Cited

OTHER PUBLICATIONS

Reagen-Shaw et al. in The FASEB Journal 22, 659-661 (2007) (Year: 2007).*

Mavlyutov et al. in Molecular Vision; 17:1034-1043 (2011) (Year: 2011).*

Smith et al. in Invest Ophthalmol Vis Sci. 2008;49: 4154-4161 (Year: 2008).*

Salhom et al. in Molecular Psychiatry (2013) 18, 12-14 (Year: 2013).*

NCT02006472_Safety And Efficacy of Pridopidine in Patients with Huntington's Disease at www.clinical trials.gov/ct2/show/NCT02006472 (2013) (Year: 2013).*

Ponten et al. in European Journal of Pharmacology 698 (2013) 278-285 (Year: 2013).*

Squitieri et al. Drug Design, Development and Therapy 2015:9 5827-5833 (Year: 2015).*

Owens et al. in The Journal of Pharmacology and Experimental Therapeutics 283(3), 1305-1322 (1997) (Year: 1997).*

Sahlholm et al., "The dopamine stabilizers ACR16 and (−)-OSU6162 display nanomolar affinities at the sigma-1 receptor," Mol. Psychiatry 2013;18(1):2-14. PMID: 22349783. (Year: 2013).*

Ponten et al., "The dopaminergic stabilizer pridopidine decreases expression of L-DOPA-induced locomotor sensitisation in the rat unilateral 6-OHDA model," Eur. J. Pharmacol. 2013;698(1-3):278-85. PMID: 23127496. (Year: 2013).*

International Search Report dated May 10, 2017 in connection with PCT International Application No. PCT/US2017/019266.

Written Opinion of the International Searching Authority dated May 10, 2017 in connection with PCT International Application No. PCT/US2017/019266.

Michal Skrzycki et al., "Multiple Protective Functions of Sigmal Receptor", *Current Protein & Peptide Science*, 2016, vol. 15, Issue 8, abstract.

Timur A. Mavlyutov et al., "Subcellular Localization of the Sigma-1 Receptor in Retinal Neurons—an Electron Microscopy Study", *Scientific Reports*, Jun. 2, 2015, 5:10689.

Brett H. Mueller II et al., "Sigma-1 receptor stimulation protects retinal ganglion cells from ischemia-like insult through the activation of extracellular-sigma regulated kinases 1/2", *Experimental Eye Research*, Oct. 2014.

Kristoffer Sahlholm et al., "Pridopidine selectively occupies sigma-1 rather than dopamine D2 receptors at behaviorally active doses", *Psychopharmacology*, 2015, 232:3443-3453.

Masamitsu Shimazawa et al. "Effect of a sigma-1 receptor agonist, cutamesine dihydrochloride (SA4503), on photoreceptor cell death against light-induced damage", *Experimental Eye Research*, Mar. 2015, abstract.

Ferdinando Squitieri et al., "Profile of pridopidine and its potential in the treatment of Huntington disease: the evidence to date", *Drug Design, Development and Therapy*, 2015:9 5827-5833.

Extended European Search Report for EP 17757261.7 dated Jun. 6, 2019.

Ponten, H., et al. (2010). In vivo pharmacology of the dopaminergic stabilizer pridopidine. European journal of pharmacology, 644(1-3), 88-95.

Dyhring, Tino, et al. The dopaminergic stabilizers pridopidine (ACR16) and (−)-OSU6162 display dopamine D2 receptor antagonism and fast receptor dissociation properties. European journal of pharmacology, 2010, 628.1-3: 19-26.

Ryskamp, Daniel, et al. The sigma-1 receptor mediates the beneficial effects of pridopidine in a mouse model of Huntington disease. Neurobiology of disease, 2017, 97: 46-59.

Bermack, J. E. et al. (2005)—Distinct modulatory roles of sigma receptor subtypes on glutamatergic responses in the dorsal hippocampus—Synapse, 55(1), 37-44.

Cantarella, G. et al. (2007)—Protective effects of the sigma agonist Pre-084 in the rat retina—British journal of ophthalmology, 91(10), 1382-1384.

Chou, Y. C. et al.(1999)—Binding of dimemorfan to sigma-1 receptor and its anticonvulsant and locomotor effects in mice, compared with dextromethorphan and dextrorphan—Brain research, 821(2), 516-519.

De Yebenes, J. G. et al. (2011)—Pridopidine for the treatment of motor function in patients with Huntington's disease (MermaiHD): a phase 3, randomized, double-blind, placebo-controlled trial—The Lancet Neurolog, vol. 10, not 12, p. 1049-1057.

Francardo, V. et al. (2014)—Pharmacological stimulation of sigma-1 receptors has neurorestorative effects in experimental parkinsonism—Brain, 137(7), 1998-2014.

Geva, M et al. (2016)—Pridopidine activates neuroprotective pathways impaired in Huntington Disease—Human molecular genetics, 25(18), 3975-3987.

Gundlach, A. L. et al. (1986)—Autoradiographic localization of sigma receptor binding sites in guinea pig and rat central nervous system with (+) 3H-3-(3-hydroxyphenyl)-N-(1-propyl) piperidine—Journal of Neuroscience, 6(6), 1757-1770.

Gupta, Divakar et al. (2016)—Glaucoma—American Family Physician,vol. 93,No. 8,668-674.

Hayashi, T. et al. (2005)—The sigma receptor: evolution of the concept in neuropsychopharmacology—Current neuropharmacology, 3(4), 267-280.

Hayashi, T. et al. (2001)—Regulating ankyrin dynamics: Roles of sigma-1 receptors—Proceedings of the National Academy of Sciences, 98(2), 491-496.

Hong, W. et al. (2004)—Modulation of bradykinin-induced calcium changes in SH-SY5Y cells by neurosteroids and sigma receptor ligands via a shared mechanism—Synapse, 54(2), 102-110.

Huntington Study Group Hart Investigators (2013)—A randomized, double-blind, placebo-controlled trial of pridopidine in Huntington's disease—Movement Disorders, vol. 28, not 10, pp. 1407-1415. First published Feb. 28, 2013.

Hyrskyluoto, A. et al. (2013)—Sigma-1 receptor agonist PRE084 is protective against mutant huntingtin-induced cell degeneration: involvement of calpastatin and the NF-$_\kappa$B pathway—Cell death & disease, 4(5), e646-e646.

Lucas, G. et al. (2008)—Further evidence for an antidepressant potential of the selective δ1 agonist SA 4503: electrophysiological, morphological and behavioural studies—International Journal of Neuropsychopharmacology, 11(4), 485-495.

Luedtke, R. R. et al. (2012)—Neuroprotective effects of high affinity sigma 1 receptor selective compounds—Brain research, 1441, 17-26.

Matsuno, K. et al. (1992)—Increase of extracellular acetylcholine level in rat frontal cortex induced by (+) N-allylnormetazocine as measured by brain microdialysis—Brain research, 575(2), 315-319.

Matsuno, K. et al.(1993)—Similar ameliorating effects of benzomorphans and 5-HT 2 antagonists on drug-induced impairment of passive avoidance response in mice: comparison with acetylcholinesterase inhibitors—Psychopharmacology, 112(1), 134-141.

Matsuno, K. et al.(1994)—Ameliorating effects of σ receptor ligands on the impairment of passive avoidance tasks in mice: involvement in the central acetylcholinergic system—European journal of pharmacology, 261(1-2), 43-51.

Maurice, T. et al. (2001)—The interaction between neuroactive steroids and the σ1 receptor function: behavioral consequences and therapeutic opportunities—Brain Research Reviews, 37(1-3), 116-132.

Maurice, T. et al.(1994)—Behavioral evidence for a modulating role of σ ligands in memory processes. I. Attenuation of dizocilpine (MK-801)-induced amnesia—Brain research, 647(1), 44-56.

Maurice, T.(1997)—Neuroprotective and anti-amnesic potentials of sigma (σ) receptor ligands—Progress in Neuro-Psychopharmacology and Biological Psychiatry, 21(1), 69-102.

Monnet, F. P. (2005)—Sigma-1 receptor as regulator of neuronal intracellular Ca2+: clinical and therapeutic relevance—Biology of the Cell, 97(12), 873-883.

Monnet, F. P. et al. (1992)—Neuropeptide Y potentiates the N-methyl-D-aspartate response in the CA3 dorsal hippocampus. II. Involvement of a subtype of sigma receptor—Journal of Pharmacology and Experimental Therapeutics, 263(3), 1219-1225.

(56) References Cited

OTHER PUBLICATIONS

Monnet, F. P. et al.(1990)—N-methyl-D-aspartate-induced neuronal activation is selectively modulated by σ receptors—European journal of pharmacology, 179(3), 441-445.
Monnet, F. P. et al.(1992)—Modulation by sigma ligands of N-methyl-D-aspartate-induced [3 H] noradrenaline release in the rat hippocampus: G-protein dependency-Naunyn-Schmiedeberg's archives of pharmacology, 346(1), 32-39.
Monnet, F. P. et al.(2006)—The σ1 protein as a target for the non-genomic effects of neuro (active) steroids: molecular, physiological, and behavioral aspects. Journal of pharmacological sciences, 100, 93-118.
Ola, M. S. et al. (2001)—Expression pattern of sigma receptor 1 mRNA and protein in mammalian retina—Molecular brain research, 95(1-2), 86-95.
Pande A.C. et al. (1999). A placebo-controlled trial of igmesine in the treatment of major depression. *European Neuropsychopharmacology*, (9), 138.
Rabinovich-Guilatt et al. (2016)—The effect of mild and moderate renal impairment on the pharmacokinetics of pridopidine, a new drug for Huntington's disease—British journal of clinical pharmacology, 81(2), 246-255.
Rousseaux, C. G., & Greene, S. F. (2016). Sigma receptors [σ Rs]: biology in normal and diseased states. Journal of Receptors and Signal Transduction, 36(4), 327-388.
Smith, S. B. et al. (2008)—In vivo protection against retinal neurodegeneration by sigma receptor 1 ligand (+)-pentazocine—Investigative ophthalmology & visual science, 49(9), 4154-4161.
Urani, A. et al. (2004)—Enhanced antidepressant efficacy of σ1 receptor agonists in rats after chronic intracerebroventricular infusion of β-amyloid-(1-40) protein—European journal of pharmacology, 486(2), 151-161.
Volz, H. P. et al.(2004)—Clinical trials with sigma ligands—Pharmacopsychiatry, 37(S 3), 214-220.
Wang, J. et al.(2016)—Activation of the molecular chaperone, sigma 1 receptor, preserves cone function in a murine model of inherited retinal degeneration—Proceedings of the National Academy of Sciences, 113(26), E3764-E3772.
Wang, J. et al.(2016)—Role of Sigma 1 Receptor in retinal degeneration of the Ins2Akita/+ murine model of diabetic retinopathy—Investigative Ophthalmology & Visual Science, 57(6), 2770-2781.
Hiramatsu, Masayuki; Hoshino, Takashi. Improvement of memory impairment by (+)-and (−)-pentazocine via sigma, but not kappa opioid receptors. *Brain research*, 2005,1057.1-2: 72-80.
Jiménez-Jiménez, Félix Javier; Ortí-Pareja, Miguel; Zurdo, José Martin, Aggravation of glaucoma with fluvoxamine. *Annals of Pharmacotherapy*, 2001, 35.12: 1565-1566.
Johnston, Tom H., et al. Pridopidine, a clinic-ready compound, reduces 3, 4-dihydroxyphenylalanine-induced dyskinesia in Parkinsonian macaques. *Movement Disorders*, 2019, 34.5: 708-715.
Kamei, Junzo. Folia Pharmacologica Japonica, 1999, vol. 114, No. 1, pp. 35-41.
Van Niel, J. C. G.; et al. Efficacy of full μ-opioid receptor agonists is not impaired by concomitant buprenorphine or mixed opioid agonists/antagonists—preclinical and clinical evidence. *Drug research*, 2015, 65.11: 562-570.
Zelefsky, Joseph R., et al. Escitalopram-induced uveal effusions and bilateral angle closure glaucoma. *American journal of ophthalmology*, 2006, 141.6: 1144-1147.
Ahmad, Saeed. Letters to the Editor: Fluoxetine and glaucoma. Annals of Pharmacotherapy, 1991, vol. 25, 436.
Geva, M., et al (2021). Neuroprotection of retinal ganglion ceiis by the sigma-1 receptor agonist pridopidine in models of experimental glaucoma. Scientific reports, 11(1), 1-16.

Hiramatsu, Masayuki et al. Improvement of memory impairment by (+)-and (−)-pentazocine via sigma, but not kappa opioid receptors. Brain research, 2005, 1057.1-2: 72-80.
Husain, S., et al. (2009). Opioid receptor-activation: retina protected from ischemic injury. Investigative ophthalmology & visual science, 50(8), 3853-3859.
Husain, S., et al. (2012). Non-analgesic effects of opioids: neuroprotection in the retina. Current pharmaceutical design, 18(37), 6101-6108.
Husain, S., et al. (2014), Regulation of nitric oxide production by δ-opioid receptors during glaucomatous injury. PLoS One, 9(10), e110397.
Jiménez-Jiménez, Felix Javier, et al. Aggravation of glaucoma with fluvoxamine. Annals of Pharmacotherapy, 2001, 35.12: 1565-1566.
Kalesnykas, G., et al. (2012). Retinal ganglion ceil morphology after optic nerve crush and experimental glaucoma, investigative ophthalmology & visual science, 53(7), 3847-3857.
Katavic, P. L., et al. (2007), Flavonoids as opioid receptor ligands: identification and preliminary structure—Activity relationships. Journal of natural products, 70(8), 1278-1282.
Lima, L., et al. Serotonin inhibits outgrowth of goldfish retina and impairs the trophic effect of taurine. Journal of neuroscience research, 1994, 38.4: 444-450.
Lopes De Faria, J. M. L., et al. (2019). δ Opioid receptor agonism preserves the retinal pigmented epithelial cell tight junctions and ameliorates the retinopathy in experimental diabetes, Investigative Ophthalmology & Visual Science, 60(12), 3842-3853.
Mclenachan, S., et al. (2013). Absence of clinical correlates of diabetic retinopathy in the Ins2Akita retina. Clinical & experimental ophthalmology, 41(6), 582-592.
Saitoh, A., et al. (2004). Potential anxiolytic and antidepressant-like activities of SNC80, a selective δ-opioid agonist, in behavioral models in rodents. Journal of pharmacological sciences, 95(3), 374-380.
Soto, I., et al. (2014). DBA/2J mice are susceptible to diabetic nephropathy and diabetic exacerbation of IOP elevation. PloS one, 9(9), e107291.
Sun, Xian, et al. Pregnenolone sulfate decreases intraocular pressure and changes expression of sigma receptor in a model of chronic ocular hypertension. Molecular biology reports, 2012, 39.6: 6607-6614.
Upton, A. L., et al. (1999). Excess of serotonin (5-HT) alters the segregation of ipsilateral and contralateral retinal projections in monoamine oxidase A knock-out mice: possible role of 5-HT uptake in retinal ganglion cells during development. Journal of Neuroscience, 19(16), 7007-7024.
Van Niel, J. C. G.; et al. Efficacy of full μ-opiold receptor agonists is not impaired by concomitant buprenorphine or mixed opioid agonists/antagonists—preclinical and clinical evidence. Drug research, 2016, 66.11: 562-570.
Volpe, D. A., et al. (2011). Uniform assessment and ranking of opioid mu receptor binding constants for selected opioid drugs. Regulatory Toxicology and Pharmacology, 59(3), 385-390.
Wang, Jing, et al. Comparison of Sigma 1 Receptor Ligands SA4503 and PRE084 to (+)-Pentazocine in the rd10 Mouse Model of RP. Investigative ophthalmology & visual science, 2020, 61.13: 3-3.
Zelefsky, Joseph R., et al. Escitalopram-induced uveal effusions and bilateral angle closure glaucoma. American journal of ophthalmology, 2006,141.6: 1144-1147.
Rodríguez-Labrada, R., et al. (2019). Eye movement abnormalities in neurodegenerative diseases. Eye Motility. DOI: http://dx.doi.org/10.5772/intechopen.81948.
Weinreb, R. N., et al. (2014). The pathophysiology and treatment of glaucoma: a review. Jama, 311(18), 1901-1911.

\* cited by examiner

Left/Normal Eye  Right/Disease Eye

TREATMENT OF NEURODEGENERATIVE EYE DISEASE USING PRIDOPIDINE

This application is a § 371 national stage of PCT International Application No. PCT/US2017/019266, filed Feb. 24, 2017, and claims the benefit of U.S. Provisional Application No. 62/299,290, filed Feb. 24, 2016, the entire contents of each of which are hereby incorporated by reference herein.

Throughout this application, various publications are referred to by first author and year of publication. Full citations for these publications are presented in a References section immediately before the claims. Disclosures of the publications cited in the References section are hereby incorporated by reference in their entireties into this application in order to more fully describe the state of the art as of the date of the invention described herein.

BACKGROUND

Glaucoma is a group of ocular diseases characterized by progressive damage to the eye at least partly due to elevated intraocular pressure (IOP) (Merck Manual of Diagnosis and Therapy (1999)). Additionally, glaucoma is characterized by retinal ganglion cell (RGC) death, axon loss and an excavated appearance of the optic nerve head (Alward 1998). The classification of glaucoma includes several subtypes including for example, primary angle-closure glaucoma, secondary open-angle glaucoma, steroid-induced glaucoma, traumatic glaucoma, pigmentary dispersion syndrome, pseudoexfoliation syndrome, secondary angle-closure glaucoma, neovascular glaucoma, uveitis, and glaucoma and other eye pathologies. Other neurodegenerative diseases of the eye include different forms of macular degeneration, retinitis pigmentosa and all types of optic neuropathy.

Glaucoma can be diagnosed before vision loss occurs by visual field testing and by ophthalmoscopic examination of the optic nerve to detect "cupping." The mean IOP in normal adults is 15 to 16 mm Hg; the normal range is 10 to 21 mm Hg. One form of management of glaucoma is based on lowering the IOP using topically applied medications (Coleman 1999).

Glaucomatous optic neuropathy appears to result from specific pathophysiological changes and subsequent death of RGCs and their axons. The process of RGC death is thought to be biphasic: a primary injury responsible for initiation of damage followed by a slower, secondary degeneration attributable to the hostile environment surrounding the degenerating cells (Kipnis et al. 2000).

The molecular mechanism triggering RGC death has not been identified. Deprivation of neurotrophic factors, ischemia, chronic elevation of glutamate or amyloid beta oligomers and disorganized nitric oxide metabolism are suspected to be possible mechanisms (Farkas et al. 2001). In addition, it is possible that the mechanisms leading to RGC death share common features with other types of neuronal injury, such as signaling by reactive oxygen species, depolarization of mitochondria, or induction of transcriptionally regulated cell death (Weinreb et al. 1999).

Pridopidine

Pridopidine (formerly ACR16, Huntexil®) is a unique compound developed for the treatment of patients with motor symptoms associated with Huntington's disease. The chemical name of pridopidine is 4-(3-(Methylsulfonyl)phenyl)-1-propylpiperidine, and its Chemical Registry Number is CAS 346688-38-8 (CSID:7971505, 2016). The Chemical Registry number of pridopidine hydrochloride is 882737-42-0 (CSID:25948790 2016). Processes of synthesis of pridopidine and a pharmaceutically acceptable salt thereof are disclosed in U.S. Pat. No. 7,923,459 and PCT Application Publication No. WO 2017/015609. U.S. Pat. No. 6,903,120 claims pridopidine for the treatment of Parkinson's disease, dyskinesias, dystonias, Tourette's disease, iatrogenic and non-iatrogenic psychoses and hallucinoses, mood and anxiety disorders, sleep disorder, autism spectrum disorder, ADHD, Huntington's disease, age-related cognitive impairment, and disorders related to alcohol abuse and narcotic substance abuse.

The effects of pridopidine on neurodegenerative eye diseases, in particular glaucoma, have not previously been reported.

SUMMARY OF THE INVENTION

The subject invention provides a method of treating a subject afflicted with a neurodegenerative eye disease comprising administering to the subject an amount of pridopidine effective to treat the subject.

The subject invention also provides a method of preventing or reducing retinal ganglion cell damage or loss in a subject, comprising administering to the subject an amount of pridopidine effective to prevent or reduce retinal ganglion cell damage or loss in the subject.

The subject invention provides a method of treating a subject afflicted with a neurodegenerative eye disease comprising administering to the subject an amount of pridopidine effective to provide neuroprotection to a retinal ganglion cell in the subject.

The subject invention also provides a package comprising:
  a) a first pharmaceutical composition comprising an amount of pridopidine; and
  b) instructions for use of the pharmaceutical composition to treat a subject afflicted with a neurodegenerative eye disease.

The subject invention also provides a therapeutic package for dispensing to, or for use in dispensing to, a subject afflicted with a neurodegenerative eye disease, which comprises:
  a) one or more unit doses, each such unit dose comprising an amount of pridopidine thereof, wherein the amount of said pridopidine in said unit dose is effective, upon administration to said subject, to treat the subject, and
  b) a finished pharmaceutical container therefor, said container containing said unit dose or unit doses, said container further containing or comprising labeling directing the use of said package in the treatment of said subject.

The subject invention also provides a pharmaceutical composition comprising an amount of pridopidine for treating a subject afflicted with a neurodegenerative eye disease.

The subject invention also provides a pharmaceutical composition comprising an amount of pridopidine for use in treating a subject afflicted with a neurodegenerative eye disease.

The subject invention also provides a pharmaceutical composition comprising pridopidine for use in a combination therapy together with a pharmaceutical composition comprising a second agent for the treatment of a neurodegenerative eye disease.

The subject invention also provides a pharmaceutical composition comprising an amount of pridopidine for use in treating a subject afflicted with a neurodegenerative eye disease as an add-on therapy or in combination with a second agent for the treatment of a neurodegenerative eye disease.

The subject invention also provides a pharmaceutical composition in a unit dosage form, useful in treating a subject afflicted with a neurodegenerative eye disease, which comprises an amount of pridopidine or pharmaceutically acceptable salt thereof, wherein the amount of said pridopidine in said composition is effective, upon administration to said subject of one or more of said unit dosage forms of said composition, to treat the subject.

Further provided is pridopidine for use in treating a subject afflicted with a neurodegenerative eye disease.

Provided herein is pridopidine for the manufacture of a medicament for use in treating a subject afflicted with a neurodegenerative eye disease.

BRIEF DESCRIPTION OF THE FIGURES

The figures are photographs of Brn-3a stained eye sections. In all the figures, the three upper panels are representative sections of Brn-3a stained healthy eyes and the three lower panels are representative sections of Brn-3a stained Hypertonic Saline injection (HSI) treated eyes.

DETAILED DESCRIPTION OF THE INVENTION

The subject invention provides a method of treating a subject afflicted with a neurodegenerative eye disease comprising administering to the subject an amount of pridopidine effective to treat the subject.

In one embodiment, the administration of pridopidine is effective to reduce or inhibit a symptom of the neurodegenerative eye disease in the subject.

In an embodiment, the neurodegenerative eye disease is selected from the group consisting of glaucoma, Age-related Macular Degeneration, optic neuropathy, and retinitis pigmentosa.

In one embodiment, the neurodegenerative eye disease is glaucoma. In another embodiment, the neurodegenerative eye disease is Wet Age-related Macular Degeneration ("Wet AMD") or Dry Age-related Macular Degeneration ("Dry AMD"). In a further embodiment, the neurodegenerative eye disease is Leber hereditary optic neuropathy (LHON).

In one embodiment, the symptom is retinal ganglion cell damage or retinal ganglion cell loss.

In one embodiment, the method comprises reducing retinal ganglion cell loss or damage in the subject.

In one embodiment, the amount of pridopidine is effective to reduce or prevent retinal ganglion cell loss or damage in the subject. In another embodiment, the retinal ganglion cell loss is reduced by at least 10%, by at least 20%, by at least 30%, by at least 40% or by at least 50%. In a further embodiment, the retinal ganglion cell loss is reduced by more than 50%, more than 60%, more than 70%, or more than 80%.

In one embodiment, treating comprises improving retinal ganglion cell viability in the patient by more than 50%, more than 60%, more than 70%, or more than 80%.

In another embodiment, treating comprises reducing retinal ganglion cell loss in the patient by more than 50%, more than 60%, more than 70%, or more than 80%.

The subject invention also provides a method of preventing or reducing retinal ganglion cell damage or loss in a subject, comprising administering to the subject an amount of pridopidine effective to prevent or reduce retinal ganglion cell damage or loss in the subject. In one embodiment, the amount of pridopidine is effective to improve retinal ganglion cell viability in a subject. In another embodiment, the amount of pridopidine is effective to protect a retinal ganglion cell from cell death in the subject. In some embodiments, the cell death is induced by elevated intraocular pressure.

In another embodiment, treating comprises slowing progression of the neurodegenerative disease of the eye in the subject. In some embodiments, the treating comprises slowing progression of visual field loss towards blindness in a patient afflicted with glaucoma. In some embodiments, treating comprises preventing blindness in a patient afflicted with glaucoma.

In one embodiment, pridopidine is pridopidine hydrochloride.

For the methods and use disclosed herein, the route of administration can be, e.g., oral. Routes of administration can also be classified by whether the effect is local (e.g., in topical administration) or systemic (e.g., in enteral or parenteral administration). "Local administration" as used herein shall mean administration of a compound or composition directly to where its action is desired, and specifically excludes systemic administration. "Topical administration" of a compound or composition as used herein shall mean application of the compound or composition to body surfaces such as the skin or mucous membranes such as eyes. "Ocular administration" as used herein shall mean application of a compound or composition to the eye of a subject or to the skin around the eye (periocular skin) or the mucosa around the eye, specifically the conjunctiva of a subject, i.e., local administration. Examples of ocular administration include topical administration directly to the eye, topical application to the eye lid or injection into a portion of the eye or eye socket. In addition, an "ocular pharmaceutical composition" as used herein means a pharmaceutical composition formulated for ocular administration. The amount of pridopidine and the pharmaceutical compositions of the present invention may be administered by oral administration, topical administration, systemic administration, local administration, or ocular administration.

In one embodiment, the pridopidine is administered via systemic administration. In some embodiments, the pridopidine is administered via oral administration.

In another embodiment, the pridopidine is administered in the form of an aerosol, an inhalable powder, an injectable, a liquid, a gel, a cream, a solid, a capsule or a tablet.

In one embodiment, the pridopidine is administered via local administration to the eye. In another embodiment, the pridopidine is administered via topical administration. In a further embodiment, the pridopidine is administered via intraocular, periocular, or ocular administration. In some embodiments, the pridopidine is administered in the form of a liquid, a gel, a cream or a contact lens.

In another embodiment, the pridopidine is administered directly to the eye of a subject, for example as eye drops, an intraocular depot injection, eye gels, a tablet inserted into the conjunctiva, or a lens loaded with pridopidine. In an embodiment, pridopidine hydrochloride is administered to the eye of the subject.

In one embodiment, the pridopidine is part of a formulation suitable to be administered by ocular drops. The ocular drops can be in the form of a liquid or a gel, preferably in the form of a liquid. When pridopidine is administered topically in the form of a liquid or gel to the eye, a lower amount of pridopidine is required to produce the same clinical effect as systemic administration of pridopidine.

In one embodiment, the amount of pridopidine administered systemically is 22.5 mg/day-315 mg/day, 90 mg/day-315 mg/day, 90-250 mg/day, or 90-180 mg/day. In another embodiment, the amount of pridopidine administered is about 22.5 mg/day, about 45 mg/day, about 67.5 mg/day, about 90 mg/day, about 100 mg/day, about 112.5 mg/day, about 125 mg/day, about 135 mg/day, about 150 mg/day, about 180 mg/day, about 200 mg/day, about 225 mg/day, about 250 mg/day, or about 315 mg/day.

In one embodiment, the amount of pridopidine administered systemically in a dose is about 22.5 mg, about 45 mg, about 67.5 mg, about 90 mg, about 100 mg, about 112.5 mg, about 125 mg, about 135 mg, about 150 mg, about 180 mg, about 200 mg, about 250 mg, or about 315 mg.

In another embodiment, the pridopidine is administered directly to the eye of a subject. In some embodiments, pridopidine is formulated for direct administration to the eye, for example topical administration to the eye, for example as eye drops, and the pridopidine is prepared in a dose range of 0.1 mg to 50 mg, or 0.2 mg to 20 mg.

In one embodiment, the amount of pridopidine administered locally is 0.1 mg/day-50 mg/day or 0.2 mg/day-20 mg/day. In another embodiment, the amount of pridopidine administered locally in a dose is 0.1 mg-50 mg or 0.2 mg-20 mg.

In one embodiment, pridopidine is administered periodically.

In one embodiment, pridopidine is administered daily.

In another embodiment, pridopidine is administered more often than once daily or less often than once daily. In one embodiment, pridopidine is administered more often than once daily, for example twice or thrice daily. In another embodiment, pridopidine is administered less often than once daily, for example, every other day or weekly.

In one embodiment, the periodic administration of pridopidine continues for at least 3 days, more than 30 days, more than 42 days, 8 weeks or more, at least 12 weeks, at least 24 weeks, more than 24 weeks, or 6 months or more. In some embodiments, for example, in the treatment of a subject with glaucoma, the treatment is a chronic treatment, with periodic administration of pridopidine for more than 12 months, more than 18 months, more than 24 months.

In one embodiment, the subject is a human patient.

In one embodiment, the method further comprises the administration of a second agent for the treatment of the neurodegenerative eye disease. In another embodiment, the second agent is a β-adrenergic antagonist, adrenergic agonist, parasympathomimetic agonist prostaglandin analog, or carbonic anhydrase inhibitor.

In another embodiment, the second agent reduces elevated intraocular pressure in a subject. In a further embodiment, the second agent is a prostaglandin agonist, a beta blocker, a carbonic anhydrase inhibitor, an alpha agonist, or a combination thereof. In an additional embodiment, the second agent is latanoprost, bimatoprost, travoprost ophthalmic, unoprostone ophthalmic, tafluprost, Betaxolol ophthalmic, Carteolol, timolol, levobunolol, metipranolol, Dorzolamide, brinzolamide, acetazolamide, methazolamide, brimonidine, Apraclonidine, or a combination thereof.

In one embodiment, the subject is administered a fixed-dose combination comprising pridopidine and the second agent.

The subject invention also provides a package comprising:
 a) a first pharmaceutical composition comprising an amount of pridopidine; and
 b) instructions for use of the pharmaceutical composition to treat a subject afflicted with a neurodegenerative eye disease.

In one embodiment, the package further comprising a second pharmaceutical composition comprising an amount of a second agent for the treatment of a neurodegenerative eye disease, wherein the instructions provide for use of the first and second pharmaceutical compositions together to treat a subject afflicted with a neurodegenerative eye disease.

In one embodiment, the amount of pridopidine and the amount of the second agent are prepared to be administered simultaneously, contemporaneously or concomitantly.

The subject invention also provides a therapeutic package for dispensing to, or for use in dispensing to, a subject afflicted with a neurodegenerative eye disease, which comprises:
 a) one or more unit doses, each such unit dose comprising an amount of pridopidine thereof, wherein the amount of said pridopidine in said unit dose is effective, upon administration to said subject, to treat the subject, and
 b) a finished pharmaceutical container therefor, said container containing said unit dose or unit doses, said container further containing or comprising labeling directing the use of said package in the treatment of said subject.

In one embodiment, the therapeutic package further comprising an amount of a second agent for the treatment of the neurodegenerative eye disease, wherein the respective amounts of said pridopidine and said second agent for the treatment of the neurodegenerative eye disease in said unit dose are effective, upon concomitant administration to said subject, to treat the subject.

The subject invention also provides a pharmaceutical composition comprising an amount of pridopidine for treating a subject afflicted with a neurodegenerative eye disease.

The subject invention also provides a pharmaceutical composition comprising an amount of pridopidine for use in treating a subject afflicted with a neurodegenerative eye disease.

In one embodiment, the pharmaceutical composition further comprising an amount of a second agent for the treatment of a neurodegenerative eye disease.

In one embodiment, the pridopidine and the second agent are prepared to be administered simultaneously, contemporaneously or concomitantly.

The subject invention also provides a pharmaceutical composition comprising pridopidine for use in a combination therapy together with a pharmaceutical composition comprising a second agent for the treatment of a neurodegenerative eye disease.

The subject invention also provides a pharmaceutical composition comprising an amount of pridopidine for use in treating a subject afflicted with a neurodegenerative eye disease as an add-on therapy or in combination with a second agent for the treatment of a neurodegenerative eye disease.

In one embodiment, the amount of pridopidine in the pharmaceutical composition is about 22.5 mg, about 45 mg, about 67.5, mg, about 90 mg, about 100 mg, about 112.5 mg, about 125 mg, about 135 mg, about 150 mg, about 180 mg, about 200 mg, about 250 mg, or about 315 mg.

In one embodiment, the amount of pridopidine in the pharmaceutical composition is 0.1 mg to 50 mg, or 0.2 mg to 20 mg.

The subject invention also provides a pharmaceutical composition in a unit dosage form, useful in treating a subject afflicted with a neurodegenerative eye disease, which comprises an amount of pridopidine or pharmaceutically acceptable salt thereof, wherein the amount of said pridopidine in said composition is effective, upon administration to said subject of one or more of said unit dosage forms of said composition, to treat the subject.

The invention also provides an ocular pharmaceutical composition comprising an amount of pridopidine and a pharmaceutically acceptable excipient suitable for administration to the eye.

In one embodiment, the ocular pharmaceutical composition further comprising a second agent for the treatment of the neurodegenerative eye disease. In one embodiment, the second agent for the treatment of the neurodegenerative eye disease is an antiglaucoma agent.

In another embodiment, the amount of pridopidine in the ocular pharmaceutical composition is 0.1 mg to 50 mg, or 0.2 mg to 20 mg.

In one embodiment, the ocular pharmaceutical composition is in the form of a liquid. In some embodiments, the concentration of pridopidine in the ocular pharmaceutical composition is from 0.0001 to 10.0 w/v %, 0.001 to 5 w/v %, 0.01 to 1 w/v %, 0.1% to 10 w/v %.

The invention also provides the ocular pharmaceutical composition for use in treating a neurodegenerative eye disease in a subject.

The invention further provides an eye drop comprising the pharmaceutical composition. The invention additionally provides a container comprising eye drops and the pharmaceutical composition.

The invention also provides an eye drop or a container comprising eye drops for use in the methods of this invention.

Further provided is pridopidine for use in treating a subject afflicted with a neurodegenerative eye disease.

Provided herein is pridopidine for the manufacture of a medicament for use in treating a subject afflicted with a neurodegenerative eye disease.

Terms

As used herein, and unless stated otherwise, each of the following terms shall have the definition set forth below.

As used herein, "pridopidine" means pridopidine base or a pharmaceutically acceptable salt thereof, as well as derivatives, for example deuterium-enriched version of pridopidine and salts.

A "salt thereof" is a salt of the instant compounds which have been modified by making acid or base salts of the compounds. The term "pharmaceutically acceptable salt" in this respect, refers to the relatively non-toxic, inorganic and organic acid or base addition salts of compounds of the present invention. For example, one means of preparing such a salt is by treating a compound of the present invention with an inorganic base.

"A neurodegenerative eye disease" as used herein is a disease which involves degeneration of neurosensory cells in the eye and/or of the optic nerve, including specifically retinal cells and/or their axons. Neurosensory cells include retinal ganglion cells, retinal pigment epithelium cells, cones, rods, and all other neuronal or glial cell types of the retina. Neurodegenerative eye diseases are exemplified by glaucoma, age-related macular degeneration (AMD), including wet and dry AMD, all variants of retinitis pigmentosa, optic neuropathy, including but not limited to ischemic optic neuropathy (ION), hereditary Leber hereditary optic neuropathy (LHON), and retinopathies including for example Stargardt's retinopathy.

In some embodiments, the neurodegenerative eye disease is glaucoma, including all clinical forms of glaucoma, for example, primary glaucoma or secondary glaucoma. A primary glaucoma is for example, primary open angle glaucoma (POAG), normal-tension glaucoma (NTG), primary angle-closure glaucoma (PACG), acute angle-closure glaucoma (AACG) and angle-closure glaucoma (ACG). A secondary glaucoma is for example, pseudoexfoliation glaucoma, pigmentary glaucoma, neovascular glaucoma, steroid-induced glaucoma, and treatment refractory glaucoma.

As used herein, an "amount" or "dose" of pridopidine as measured in milligrams refers to the milligrams of pridopidine (4-[3-(methylsulfonyl)phenyl]-1-propyl-piperidine) present in a preparation, regardless of the form of the preparation. For example, a unit dose containing "90 mg pridopidine" means the amount of pridopidine in a preparation is 90 mg, regardless of the form of the preparation. Thus, when in the form of a salt, e.g. pridopidine hydrochloride, the weight of the salt form necessary to provide a dose of 90 mg pridopidine would be greater than 90 mg due to the presence of the salt.

As used herein, a "unit dose", "unit doses" and "unit dosage form(s)" mean a single drug administration entity/entities.

As used herein, "about" in the context of a numerical value or range means±10% of the numerical value or range recited or claimed.

As used herein, "effective" when referring to an amount of pridopidine refers to the quantity of pridopidine that is sufficient to yield a desired therapeutic response. Efficacy can be measured by e.g., a reduced retinal ganglion cell loss or damage.

"Administering to the subject" or "administering to the (human) patient" means the giving of, dispensing of, or application of medicines, drugs, or remedies to a subject/patient to relieve, cure, or reduce the symptoms associated with a condition, e.g., a pathological condition. The administration can be periodic administration. As used herein, "periodic administration" means repeated/recurrent administration separated by a period of time. The period of time between administrations is preferably consistent from time to time. Periodic administration can include administration, e.g., once daily, twice daily, three times daily, four times daily, weekly, twice weekly, three times weekly, four times weekly and so on, etc.

As used herein, "a pharmaceutically acceptable excipient suitable for administration to the eye" includes any excipient that is known to be or expected to be suitable for administration directly to the eye.

Excipients (or additives) that are usually used in formulating ocular drops can be used together with pridopidine. Excipients may include preservatives, including quaternary ammonium salts such as benzalkonium chloride, benzethonium chloride and the like; cationic compounds such as chlorhexidine gluconate and the like; p-hydroxybenzoates such as methyl p-hydroxybenzoate, propyl p-hydroxybenzoate and the like; alcohol compounds such as chlorobutanol, benzyl alcohol and the like; sodium dehydroacetate; thimerosal; sorbic acid; and the like (U.S. Pat. No. 6,114,319). The formulation suitable to be administered by ocular drops may include a buffer, such as acetates such as sodium acetate and the like, phosphates such as sodium dihydrogenphosphate, disodium hydrogenphosphate, potassium dihydrogenphosphate, dipotassium hydrogenphosphate and the like, aminocaproic acid, amino acid salts such as sodium glutamate and the like, boric acid and salt thereof, citric acid and salt thereof, and the like (U.S. Pat. No. 6,114,319). The formulation suitable to be administered by ocular drops may include excipients, such as a stabilizer, an antioxidant, a pH adjusting agent, a chelating agent, a thickener and the like (U.S. Pat. No. 6,114,319). Examples of the antioxidant include ascorbic acid and salt thereof, sodium thiosulfate, sodium hydrogensulfite, tocopherol, sodium thiosulfate, sodium hydrogensulfite, pyruvic acid and salt thereof, and the like (U.S. Pat. No. 6,114,319). Examples of chelating agent include sodium edetate, citric acid and salt thereof, and the like (U.S. Pat. No. 6,114,319). Examples of the pH adjusting agent include hydrochloric acid, phosphoric acid, acetic acid, sodium hydroxide, sodium hydrogencarbonate, potassium hydroxide, sodium carbonate, sulfuric acid, aqueous ammonia and the like (U.S. Pat. No. 6,114,319). The pH of the formulation suitable for administration by ocular drops may be at any point within an ophthalmologically acceptable range, for example, between pH 5.0 and pH 8.0. When pridopidine is to be administered by ocular drops or eye drops, it is preferable to prepare the formulation so that the concentration of pridopidine is from 0.0001 to 10.0 w/v %.

Pharmaceutically Acceptable Salts

The active compounds for use according to the invention may be provided in any form suitable for the intended administration. Suitable forms include pharmaceutically (i.e. physiologically) acceptable salts, and pre- or prodrug forms of the compound of the invention.

Examples of pharmaceutically acceptable salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate, the phthalate, the salicylate, the sorbate, the stearate, the succinate, the tartrate, the toluene-p-sulphonate, and the like. Such salts may be formed by procedures well known and described in the art.

Pharmaceutical Compositions

While the compounds for use according to the invention may be administered in the form of the raw compound, it is preferred to introduce the active ingredients, optionally in the form of physiologically acceptable salts, in a pharmaceutical composition together with one or more adjuvants, excipients, carriers, buffers, diluents, and/or other customary pharmaceutical auxiliaries.

In an embodiment, the invention provides pharmaceutical compositions comprising the active compounds or pharmaceutically acceptable salts or derivatives thereof, together with one or more pharmaceutically acceptable carriers therefore, and, optionally, other therapeutic and/or prophylactic ingredients know and used in the art. The carrier(s) must be "acceptable" in the sense of being compatible with the other ingredients of the formulation and not harmful to the recipient thereof.

General techniques and compositions for making dosage forms useful in the present invention are described in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol. 40 (Gilbert S. Banker, Christopher T. Rhodes, Eds.). These references in their entireties are hereby incorporated by reference into this application.

"Treating" as used herein encompasses, e.g., inducing inhibition, regression, or stasis of a disease or disorder, e.g., glaucoma, or alleviating, lessening, suppressing, inhibiting, reducing the severity of, eliminating or substantially eliminating, or ameliorating a symptom of the disease or disorder. Treatment further comprises providing neuroprotection to an ocular cell, for example a retinal ganglion cell in a subject. The "neuroprotective" activity of pridopidine is disclosed herein. Neuroprotection comprises protection of neurons, for example RGC, from injury or death or b) improvement of neuronal function for example of RGC. As used herein, "neuroprotection" refers to reducing, preventing, attenuating and/or reversing progression of neurodegeneration. As used herein, "neurodegeneration" refers to the progressive loss of neurons, for example RGC, by injury or death.

"Inhibition" of disease progression or disease complication in a subject means preventing or reducing the disease progression and/or disease complication in the subject.

A "symptom" associated with glaucoma includes any clinical or laboratory manifestation associated with glaucoma and is not limited to what the subject can feel or observe.

As used herein, a subject "afflicted" with glaucoma means the subject has been diagnosed with glaucoma.

As used herein, a subject at "baseline" is as subject prior to administration of pridopidine in a therapy as described herein.

A "pharmaceutically acceptable carrier" refers to a carrier or excipient that is suitable for use with humans and/or animals without undue adverse side effects (such as toxicity, irritation, and allergic response) commensurate with a reasonable benefit/risk ratio. It can be a pharmaceutically acceptable solvent, suspending agent or vehicle, for delivering the instant compounds to the subject.

It is understood that where a parameter range is provided, all integers within that range, and tenths thereof, are also provided by the invention. For example, "0.1 mg-40.0 mg" includes 0.1 mg, 0.2 mg, 0.3 mg, 0.4 mg, etc. up to 40.0 mg.

As used herein, a "fixed-dose combination" or "fixed-dosage combination" refers to a medicament which comprises two active agents. Typically, the two agents are very difficult to separate by means readily available to patients. Non-limiting examples include tablets, pills, or solutions comprising two agents.

In this application, when a comparative term is used, such as "the retinal ganglion cell loss is reduced by at least 10% in a subject" the comparison is relative to a subject afflicted with an analogous disease for example the control subject in a prior relevant clinical study, and not to a healthy subject. For example, the retinal ganglion cell loss may be compared to the average retinal ganglion cell loss in similarly diseased subjects without treatment with pridopidine. Thus, the comparison value may be obtained by reference to the placebo group of a clinical study.

The combination of the invention may be formulated for its simultaneous, separate or sequential administration, with at least a pharmaceutically acceptable carrier, additive, adjuvant or vehicle as described herein. Thus, the combination of the two active compounds may be administered:

as a combination that is part of the same medicament formulation, the two active compounds are then administered simultaneously, or as a combination of two units, each with one of the active substances giving rise to the possibility of simultaneous, sequential or separate administration.

As used herein, "concomitant administration" or administering "concomitantly" means the administration of two agents given in close enough temporal proximately to allow the individual therapeutic effects of each agent to overlap.

As used herein, "add-on" or "add-on therapy" means an assemblage of reagents for use in therapy, wherein the subject receiving the therapy begins a first treatment regimen of one or more reagents prior to beginning a second treatment regimen of one or more different reagents in addition to the first treatment regimen, so that not all of the reagents used in the therapy are started at the same time. For example, adding pridopidine therapy to a glaucoma patient already receiving therapy with IOP reducing eye drops.

For the foregoing embodiments, each embodiment disclosed herein is contemplated as being applicable to each of the other disclosed embodiments. For instance, the elements recited in the method embodiments can be used in the pharmaceutical composition, package, and use embodiments described herein and vice versa.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Example 1: Assessment of the Neuroprotective Efficacy of Pridopidine for the Retinal Ganglion Cell (RGC) Survival in a Rat Glaucoma Model The purpose of this study is to assess the efficacy of pridopidine in protecting against chronic ocular hypertension (OHT) and/or RGC degeneration in a rat glaucoma model. Intraocular pressure (IOP) is created by injecting hypertonic saline into the episcleral veins in one eye of the Brown Norway rat. In this model ("Morrison model"), RGC degeneration occurs in response to increased IOP and chronic ocular hypertension (OHT) similar to the etiology in certain human patients with glaucoma.

The study includes 4 groups (n=8-11 each): Group 1 (3 mg/kg oral pridopidine daily, n=8), Group 2 (30 mg/kg oral pridopidine daily n=9), Group 3 (60 mg/kg oral pridopidine daily n=10), and Group 4 (vehicle, n=11).

Materials

Test Article: Pridopidine Hydrochloride in water solution.

Control Article: 0% Pridopidine Hydrochloride in water solution.

Animals

Number and Species: The study and outline-specified data are collected from Brown Norway rats (*Rattus norvegicus*). Rats have been used historically in the OHT models and there are no other approved alternative preclinical methods.

Sex: male, Weight/Age Range: approximately 225-450 grams and at least 12 weeks old (adult) weighed to nearest 0.1 g.

Procedure

The control or test article was administered orally to four groups of 8-11 animals.

Pre-Dose Administration and Selection of Animals:

Clinical observations were performed daily. Animals are weighed weekly prior to initiation of dosing.

Ophthalmic Examinations:

Animals selected for the study were examined prior to the initial administration of the test or the control articles to ensure that both eyes are free of abnormality, damage, and disease. The anterior segment evaluation of both eyes in all animals was performed and scored following Combined Draize and McDonald-Shadduck Scoring Systems. The posterior segment evaluation was performed following Posterior Segment Scoring Scale for ocular lesions. Only rats showing no signs of eye irritation, ocular defects, or pre-existing corneal injury were used in the study.

Intraocular Pressure (IOP) Measurements:

IOP was measured in wakeful animals from both eyes using a Tono-Pen Vet tonometer (Reichert, Inc.; Depew, N.Y.). Ten (10) IOP readings were recorded from each eye and averaged. IOP measurements were taken around the same time (e.g., between 10 a.m. and 2 p.m.) across measurement time-points to minimize the circadian variability of IOP. The baseline IOP measurement was performed at Week-2 (pre-dose) (IOP-1). Corneas were topically anaesthetized with 0.5% proparacaine HCl ophthalmic solution before the IOP measurements.

HSI Procedure:

The glaucoma model was created in one eye per animal through Hypertonic Saline injection (HSI) into the episcleral veins, one injection per week for two weeks (at Weeks-2 and -1) in the same eye in the study. HSI was performed under a surgical microscope. An upper or lower episcleral vein was exposed in the OHT eye and an occluder ring was placed around the eye to isolate an episcleral vein. Fifty to five-hundred micro-liters (50-500 µL) of micro-filtered Hypertonic Saline solution (NaCl, 1.8-2.0M) was injected using an Infusion Pump (Lomir Biomedical; Malone, N.Y.) into the limbal vascular plexus via the episcleral vein in the OHT eye. If used, the occluder ring was removed shortly after the saline injection. At least one week after the first HSI (at Week-2), a second HSI was performed in another episcleral vein on the same eye (at Week-1). The eye with hypertonic saline injections was designated as the OHT eye and the contralateral eye was designed as the non OHT eye.

Animal Sedation:

Animals were sedated with appropriate anesthesia using 40-80 mg/kg Ketamine and 5-10 mg/kg Xylazine (Intramuscular or Intraperitoneal injection), or 1-3% Isoflurane (Inhalation) before HSI. The surface of the eyes was treated with 0.5% erythromycin or appropriate ophthalmic ointment or balanced salt solution (BSS) during HSI. During animal sedation, the eyes were kept moist to avoid drying out. Animals were kept warm until they woke up and were returned to cages. Animals were treated with Buprenorphine 0.02-0.1 mg/kg every 8 to 12 hours (SQ or IM) twice per treatment (24 hours) and treatment was extended as needed.

Dose Administration:

Rats were separated in 4 groups. Animals in each group received one of the four following articles during the study:
- group 1: Control solution (vehicle)
- group 2: 3 mg/kg oral pridopidine daily
- group 3: 30 mg/kg oral pridopidine daily
- group 4: 60 mg/kg oral pridopidine daily Rats were dosed orally daily approximately between 8 a.m. and 10 a.m., starting on the day of the first HSI until euthanasia, which was the last day of dosing. The volume for each oral dose was 1 mL.

Post-Dose Procedures:

Clinical observations were performed at least once daily. Additionally, daily cage-side clinical observations included, but were not limited to, changes in the skin, fur, eyes and mucous membranes, respiratory system, circulatory system, autonomic central nervous system, somatomotor activity, locomotor activity, and behavior pattern. Particular attention was directed to observations of central nervous system signs (seizures, tremors, salivation), hypersensitivity, and changes in feces and/or the presence of diarrhea.

Moribund and Dead Animals:

Animals were observed once daily for moribundity/mortality as part of the clinical observations. Animals whose condition makes it unlikely that they will survive until the next observation were to be humanely euthanized and necropsied and eyeballs collected.

Measurements and Criterion:

Animals were weighed weekly and prior to euthanasia. Both eyes were examined weekly and prior to euthanasia as described above in the section titled Ophthalmic Examinations. IOP measurements were taken once weekly starting one week after the second HSI and prior to euthanasia as described above in the section entitled IOP Measurements. In total, eight (8) time points were taken (IOP-2-IOP5) post HSI administration. Each IOP measurement was performed at approximately the same time each day.

Sacrifice:

Animals were euthanized by carbon dioxide inhalation at the end of the study. Both eyes were immediately enucleated after animals were sacrificed.

Preparation of Retinas:

Both eyes were fixed in 4% paraformaldehyde fixative at 4±2° C. for at least 24 hours. Retinas were dissected and kept in phosphate buffered saline (PBS) until immunohistofluorescence.

Immunohistofluorescence:

Retinas were permeabilized in PBS-0.5% Triton X-100 by freezing at 70±12° C. for at least 1 hour, rinsed in fresh PBS-0.5% Triton X-100 and incubated overnight at 4±2° C. with the appropriate primary antibody (Brn-3a (14A6): Santa Cruz Biotechnology catalog #sc-8429; an RGC marker, Pezda, 2005) diluted in blocking buffer (PBS, 2% normal donkey serum, 2% Triton X-100). Retinas were washed three times in PBS 0.5% Triton X-100 and incubated at room temperature for 2-4 hours with fluorescence conjugated-secondary antibodies (anti-mouse IgG (H+L), Alexa Fluor 594, #A21203) diluted in blocking buffer. Finally, after washing in PBS-0.5% Triton X-100 at least 3 times, retinas were rinsed and kept in PBS at 4±2° C. for further processing.

Whole Retinal Flat Mounting:

After Immunohistofluorescence staining, four (4) radial cuts were made in the retina, and retinae were flat mounted with anti-fading solution. The slides were kept at 4±2° C. till visualization and imaging.

RGC Visualization and Imaging:

The stained RGCs in the retinas were visualized and evaluated by fluorescence microscopic examination. The stained RGCs were imaged and two areas (one medial, one distal), which are an appropriate distance away from the center of the optic nerve head, are selected in each retinal quadrant (8 regions per retina are taken). The images of the RGCs were saved for further RGC calculation.

RGC Calculation:

The stained RGCs were counted using the image analysis software Image J. The number of RGCs are expressed in the cell number per mm2.

Evaluation Criteria

The results of the study were considered in terms of the in-life and post in-life observations and any microscopic observations.

IOP Criterion:

For each time-point following the second HSI, the IOP elevation was calculated as the difference between the level in the OHT eye and that in the normal eye (non-OHT eye) or the difference IOP ($\Delta$IOP). Data was analyzed and reported for rats which did not have individual IOP measurements of greater than or equal to 50 mmHg in the OHT eyes. When $\Delta$IOP per animal was equal to or greater than 6 mmHg, OHT was created in the animal and the animal is placed into the study. Otherwise, the animal was to be removed from the study. A total of three animals were excluded due to low IOP following the HSI procedure; one from each of the vehicle group, the 3 mg/kg group and the 60 mg/kg group.

The $\Delta$IOPs of the four (4) post-dose administration IOP measurements (IOP-2-IOP-5) were averaged and constituted the Mean $\Delta$IOP for each animal. For each group, eight (8) animals with a sustained IOP elevation in the OHT eye were selected from a larger pool and groups are matched for the Mean $\Delta$IOP. Only animals with reduced IOP were evaluated for neurodegeneration. Other animals were removed from the study.

Data was analyzed and reported for rats which do not have individual IOP measurements of greater than 50 mmHg in the OHT eyes. If an individual IOP measurement in the OHT eyes was greater than 50 mmHg, the animal was to be removed from the study.

Percent (%) RGC loss in the OHT retinas was calculated in comparison to the RGC counts in the Non-OHT retina of the same animal using the following formula: [100−(100× OHT/Non-OHT Mean RGC Counts per Retina)]. The RGC counts in each Non-OHT retina were considered 100% for that animal. Animals in the vehicle control group had at least 20% loss (43% see table 1, below), thereby validating the model.

Data Analysis:

Initially One-Way ANOVA was used to address statistically significant differences among groups. In the event there was statistical significance, data of the test groups was further compared with the data of the control group using Dunnett's multiple comparison tests.

Additional or alternative statistical tests may be performed. Any differences between control and test animals was considered statistically significant only if the probability of the differences being due to chance was equal to or less than 5% (p<0.05; two-tailed). Statistical analysis was performed using Minitab, Minitab Inc, State College, Pa. Any significant difference was further assessed for biological relevance by comparison to the literature and historical data.

Results/Conclusion

A pilot study was performed for 14 days with highest dose of pridopidine to assess the effect of pridopidine on intraocular pressure. Pridopidine itself did not reduce IOP.

In the primary study, pridopidine treatment started at the day of HSI and continued for 41 days. IOP was measured weekly to make sure it sustained.

On day 41, rats were sacrificed and retina (from both eyes) were fixed. The number of RGC were counted in 8 histological sections for each retina. The results, as measured by % of retinal ganglion cell loss are presented in Table 1 and in FIGS. 1-4.

Retinal images were evaluated by confocal fluorescence microscopic examination. Number of viable RGC (stained with anti Brn-3a) were counted. Percent RGC loss in the OHT retinae was calculated in comparison to the RGC counts in the non-OHT retinae of the same animal using the following formula: (100−(100×OHT/non-OHT Mean RGC counts per retina)). The RGC counts in each non-OHT retina were considered as 100% for that animal.

Figure 1:
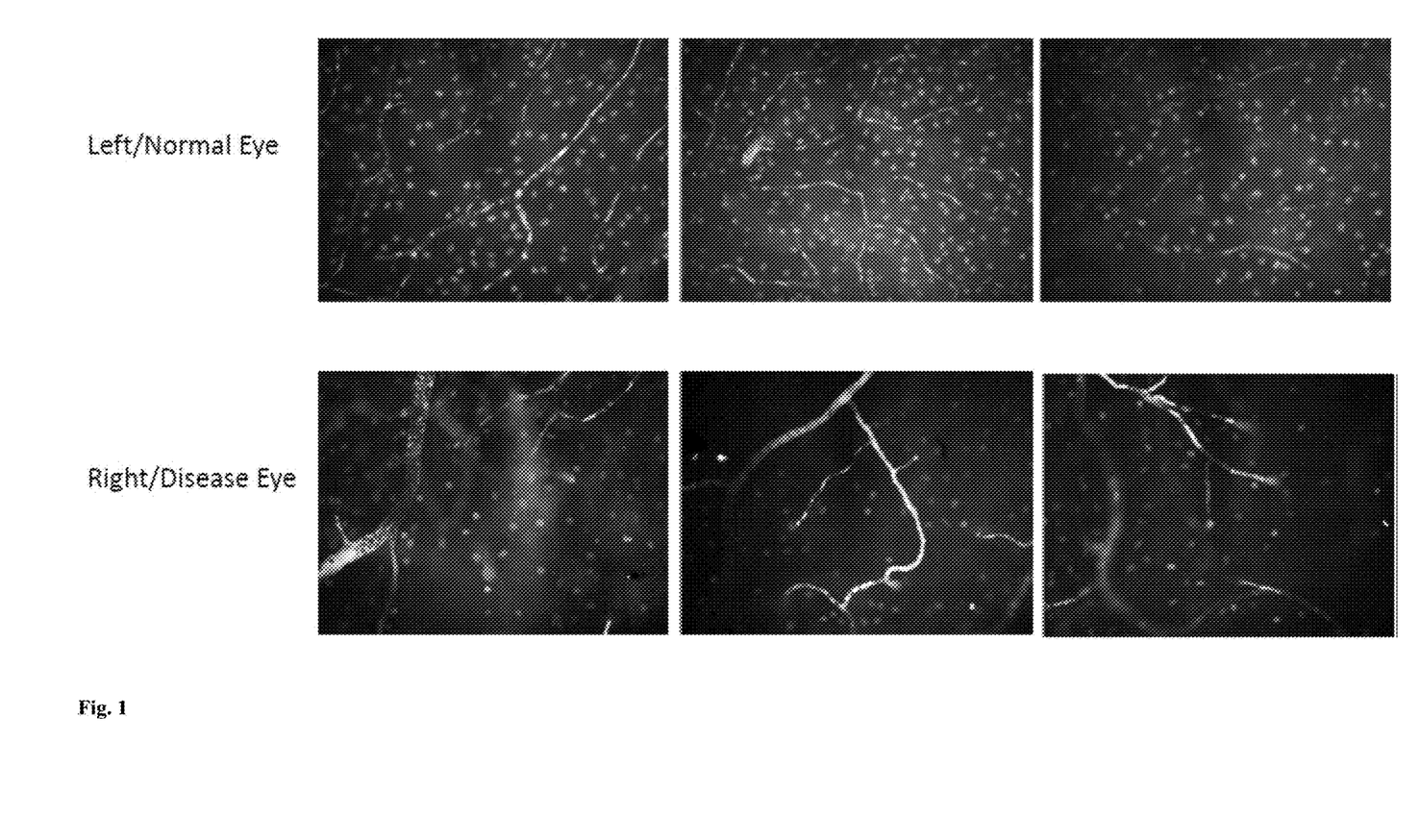
FIG. 1: Representative Immunostaining Images of Ganglion Cells Antibody: Brn-3a for Group 1-ddH2O.

In FIG. 1, in the diseased eye (lower panel) there are significantly less viable cell (bright dots) counts than in the healthy eyes (upper panels). There was a 43% RGC loss in the HSI treated eye compared to the healthy eyes.

Figure 2:
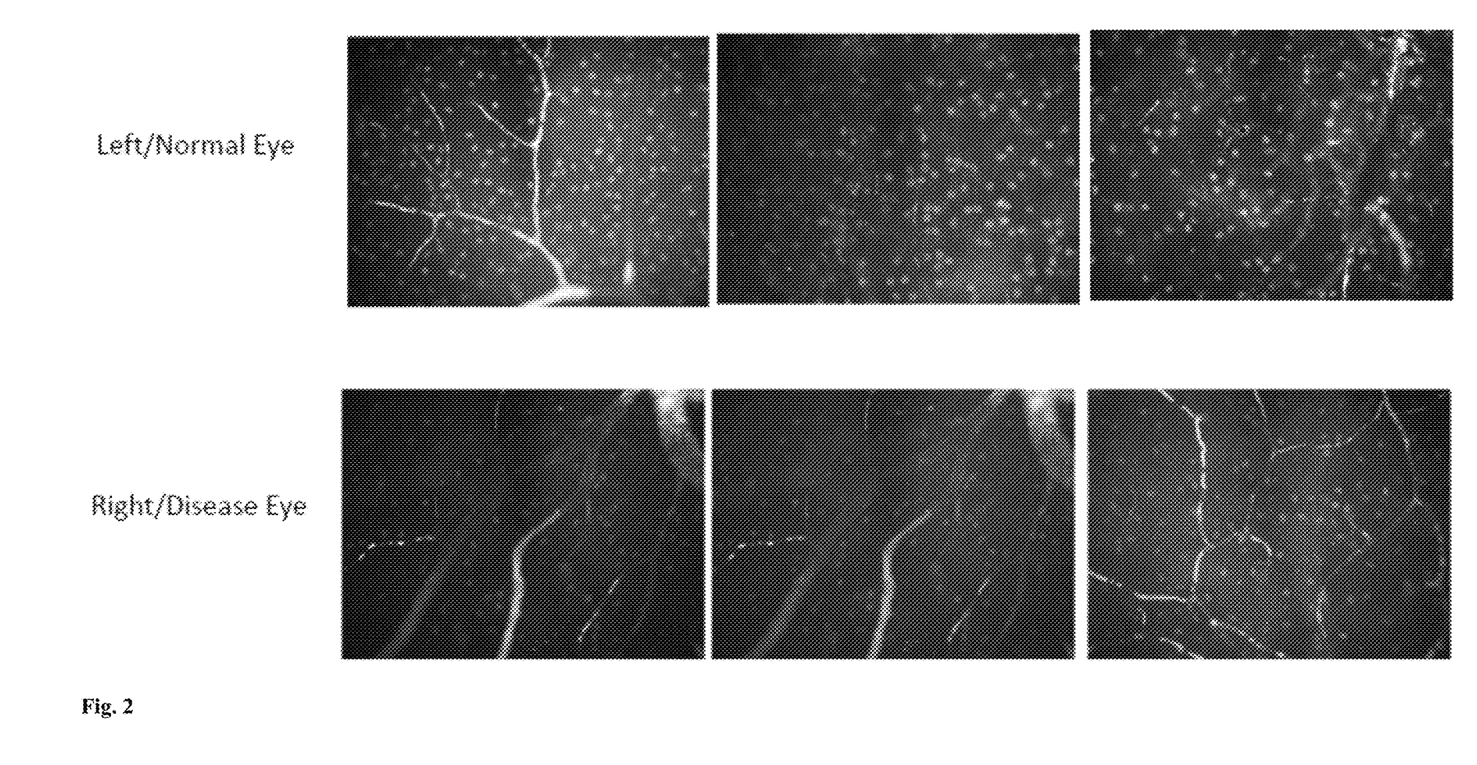
FIG. 2: Representative Immunostaining Images of Ganglion Cells Antibody: Brn-3a for Group 2-pridopidine 3 mg/kg.

In FIG. 2, in the diseased eyes (lower panel) treated with low pridopidine treatment there is only 25% RGC loss.

Figure 3:
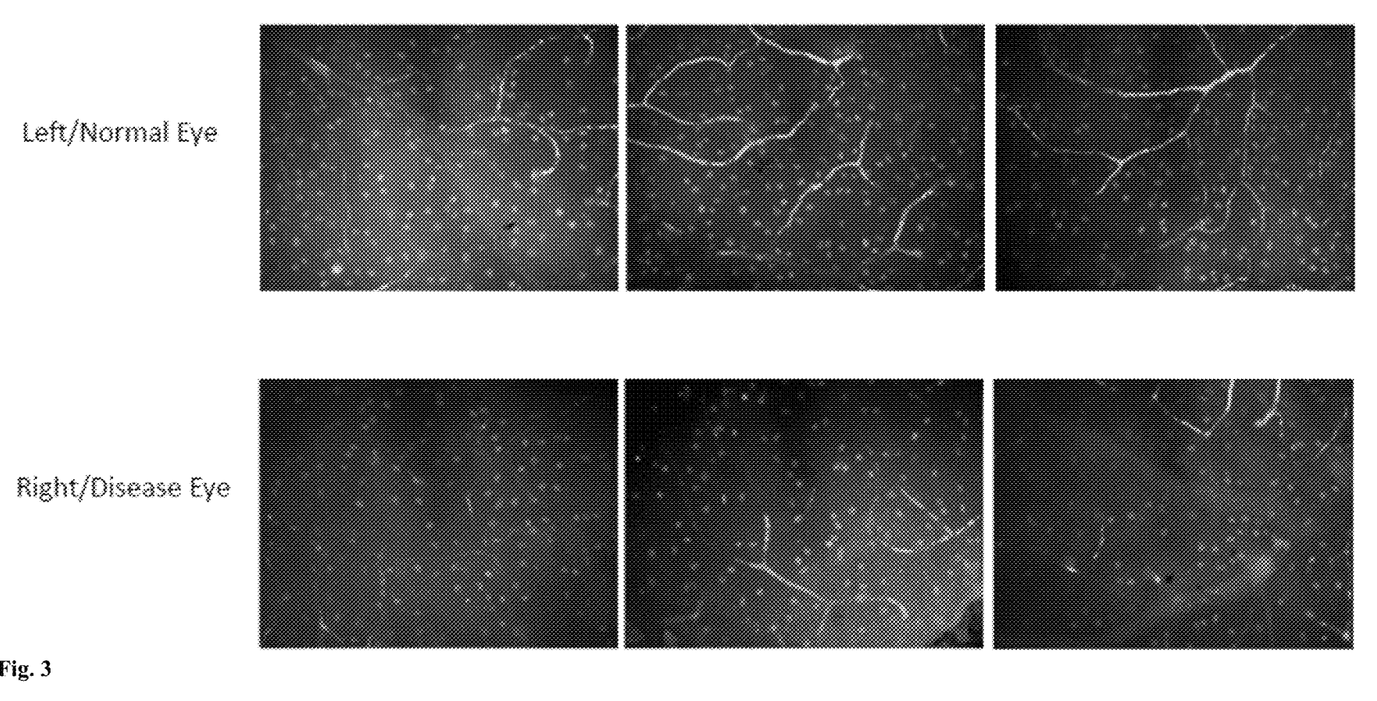
FIG. 3: Representative Immunostaining Images of Ganglion Cells Antibody: Brn-3a for Group 3-pridopidine 30 mg/kg.

In FIG. 3, in the diseased eyes (lower panel) treated with 30 mg/kg pridopidine there is only 21% RGC loss.

Figure 4:
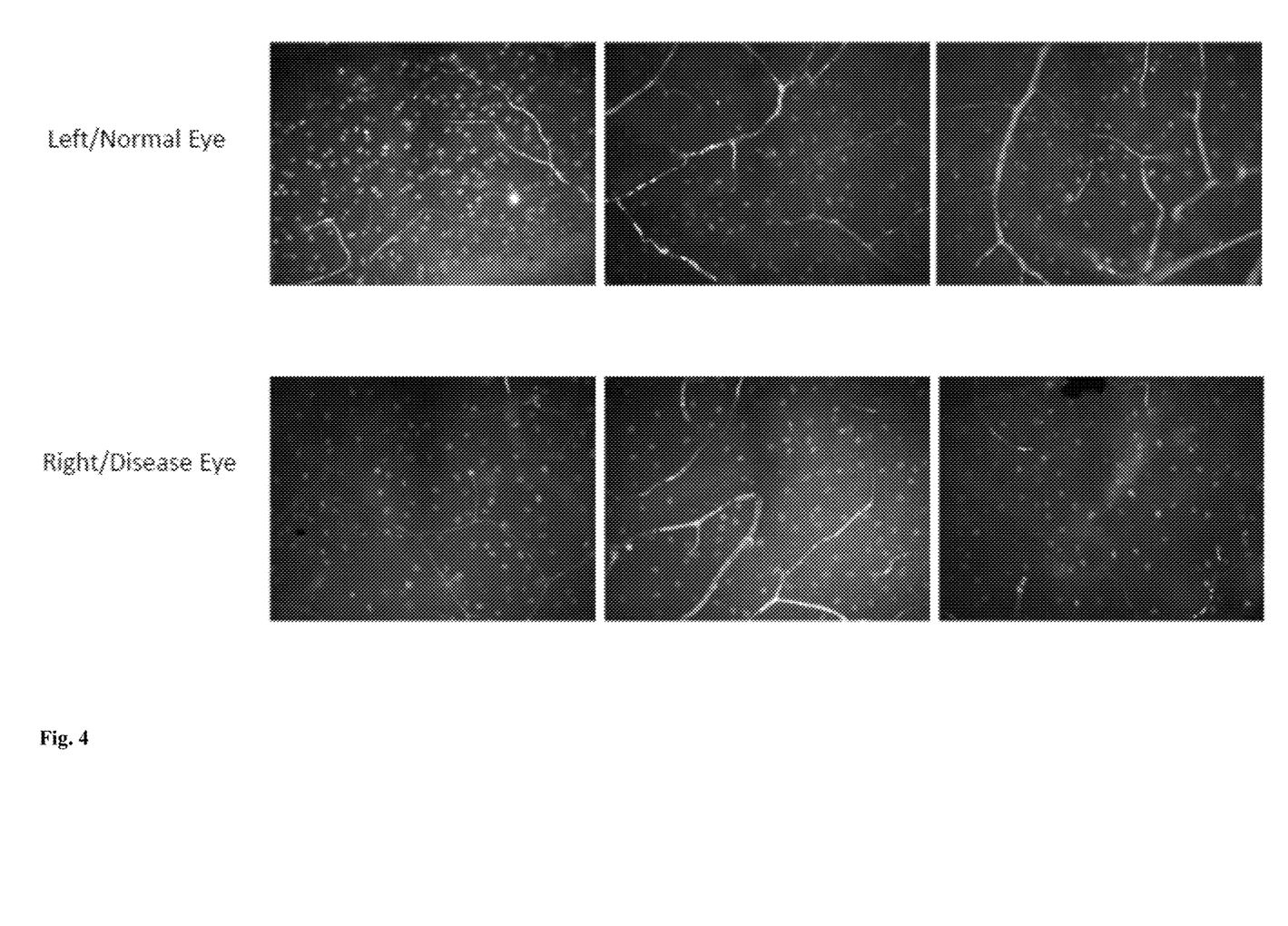
FIG. 4: Representative Immunostaining Images of Ganglion Cells Antibody: Brn-3a for Group 4-pridopidine 60 mg/kg.

In FIG. 4, in the diseased eyes (lower panel) treated with 60 mg/kg pridopidine there is only 7% RGC loss.

TABLE 1

Mean RGC loss (%) per group.

| Group | Mean RGC loss (%) per group | STDEV | # of animals per group | T-TEST |
|---|---|---|---|---|
| vehicle | 43% | 19 | 11 | |
| Pridopidine 3 mg/kg | 25% | 21 | 8 | 0.068 |
| Pridopidine 30 mg/kg | 21% | 18 | 9 | 0.019 |
| Pridopidine 60 mg/kg | 7% | 30 | 10 | 0.005 |

The data shows good neuroprotection of RGC with 3, 30 and 60 mg/kg pridopidine, and statistically significant neuroprotection of RGC with 30 and 60 mg/kg pridopidine.

Pridopidine showed a positive effect in the rat glaucoma model.

As compared to the control group rats, the rats receiving pridopidine (via oral administration) exhibited, improved RGC viability, and reduced RGC loss.

In addition, the histological examination of the optical nerve showed significantly less axonal degeneration in rats treated with pridopidine. The retinal ganglion cells' axons, which form the optic nerve, degenerate as a consequence of the death of the retinal ganglion cells. As more RGC die, more axons die which leads to the optic nerve becoming more atrophic.

Pridopidine had no effect on intraocular pressure. Pridopidine treated animals exhibited significantly increased viability of the RGCs and reduced RCG loss in a dose-dependent manner.

Pridopidine shows a positive effect in the rat glaucoma model in Example 1, supra. As compared to the control group rats, exhibiting 43% RGC loss, the rats receiving pridopidine (3, 30 and 60 mg/kg via oral administration), exhibit 24%, 21% and 7% RGC loss respectively. RGC loss in the model was significantly improved with treatment of Pridopidine at 30 mg/kg (p<0.05) and at 60 mg/kg (p<0.01).

Example 2: Topical Administration of Pridopidine

The Rat Glaucoma Model of Example 1 is performed as described above with the exception that pridopidine is topically administered to the HSI treated eye of the rats of groups 2, 3, and 4 instead of orally administered. The amount of pridopidine administered to rats in group 4 is greater than the amount of pridopidine administered in group 3 and the amount of pridopidine administered to rats in group 3 is greater than the amount of pridopidine administered to rats in group 2. Similar to Example 1, no pridopidine is administered to rats in group 1. Pridopidine significantly increases viability of the RGCs and reduces RCG loss in a dose-dependent manner in groups 2, 3 and 4 compared to group 1.

Example 3: Combination Therapy

The Rat Glaucoma Model of Example 1 is performed as described above with the exception that in addition to oral pridopidine, rats in each of Groups 1, 2, 3 and 4 are also treated with IPO reducing eye drops daily approximately between 8 a.m. and 10 a.m., starting on the day of the first HSI until euthanasia, which is the last day of dosing. This periodic administration of pridopidine in combination with IPO reducing eye drops to rats in this model provides increased efficacy (provides at least an additive effect or more than an additive effect) in treating the rats than when pridopidine is administered alone or when the IPO reducing eye drops are administered alone (at the same dose). The combination therapy also provides efficacy (provides at least an additive effect or more than an additive effect) in treating the rats without undue adverse side effects or affecting the safety of the treatment.

The combination therapy provides a clinically meaningful advantage and is more effective (provides at least an additive effect or more than an additive effect) in treating the patient than when pridopidine or IPO reducing eye drops are administered alone (at the same dose) in the following manner:

1. The combination therapy is more effective (provides an additive effect or more than an additive effect) in increasing viability of the RGCs in groups 2, 3 and 4 compared to group 1.

2. The combination therapy is more effective (provides an additive effect or more than an additive effect) in reducing RCG loss in groups 2, 3 and 4 compared to group 1.

Example 4: Assessment of Efficacy of Pridopidine for Treating Patients Afflicted with Glaucoma Long-term (e.g., daily or twice daily) administration of pridopidine (oral) is effective in treating human patients with glaucoma. Long-term (e.g., daily or twice daily) administration of pridopidine is effective to reduce a glaucoma-associated symptom in the subject.

A pridopidine composition as described herein is administered systemically to a subject or topically to the eye to of a subject suffering from glaucoma. The administration of the composition is effective to treat the subject suffering from glaucoma. The administration of the composition is also effective to reduce a glaucoma-associated symptom of glaucoma in the subject. The administration of the composition is effective to reduce RGC damage and/or RGC loss, and prevents (partly) a further shrinking of the visual filed in the subject.

Example 5: Assessment of Efficacy of Pridopidine for Treating Patients Afflicted with Dry Age-Related Macular Degeneration (AMD)

Long-term (e.g., daily or twice daily) administration of pridopidine (oral) is effective in treating human patients with dry AMD. Long-term (e.g., daily or twice daily) administration of pridopidine is effective to reduce a dry AMD-associated symptom in the subject, for example visual acuity. The decline of visual acuity that finally leads to functional blindness of the patients is attenuated or stopped. In some patients, visual acuity is partly restored. The pathological correlation for the decline of visual acuity is the progressive expansion of the degenerated area of the retina (i.e., geographic atrophy), specifically in the macula. The significantly reduced progression of the degenerative area is monitored with, for example, a computer-assisted fluorescence technique.

A pridopidine composition as described herein is administered systemically to a subject or topically to the eye of a subject suffering from dry AMD. The administration of the composition is effective to treat the subject suffering from dry AMD. The administration of the composition is also effective to reduce a dry AMD-associated symptom of dry AMD in the subject and to avoid progression of the dry form of AMD to the late stage wet form.

Example 6: Assessment of Efficacy of Pridopidine for Treating Patients Afflicted with Wet Age-Related Macular Degeneration (AMD)

Long-term (e.g., daily or twice daily) administration of pridopidine (oral) is effective in treating human patients with wet AMD. Long-term (e.g., daily or twice daily) administration of pridopidine is effective to reduce wet AMD-associated symptoms in the subject and improve eye-sight.

A pridopidine composition as described herein is administered systemically to a subject or topically to the eye of a subject suffering from wet AMD. The administration of the composition is effective to treat the subject suffering from wet AMD. The administration of the composition is also effective to reduce a wet AMD-associated symptom of wet AMD in the subject.

Example 7: Assessment of Efficacy of Pridopidine for Treating Patients Afflicted with Retinitis Pigmentosa Periodic (e.g., daily or twice daily) administration of pridopidine (oral) is effective in treating human patients with retinitis pigmentosa. Periodic (e.g., daily or twice daily) administration of pridopidine is effective to reduce a retinitis pigmentosa-associated symptom in the subject.

A pridopidine composition as described herein is administered systemically to a subject or topically to the eye of a subject suffering from retinitis pigmentosa. The administration of the composition is effective to treat the subject suffering from retinitis pigmentosa. The administration of the composition is also effective to reduce a retinitis pigmentosa-associated symptom of retinitis pigmentosa in the subject.

Example 8: Assessment of Efficacy of Pridopidine for Treating Patients Afflicted with Optic Neuropathy Long-term (e.g., daily or twice daily) administration of pridopidine (oral) is effective in treating human patients with optic neuropathy. Long-term (e.g., daily or twice daily) administration of pridopidine is effective to reduce an optic neuropathy-associated symptom in the subject.

A pridopidine composition as described herein is administered systemically to a subject or topically to the eye of a subject suffering from optic neuropathy. The administration of the composition is effective to treat the subject suffering from optic neuropathy. The administration of the composition is also effective to reduce an optic neuropathy-associated symptom of optic neuropathy in the subject.

Treatment of a subject afflicted with Leber's hereditary optic neuropathy with pridopidine in the manner of this example results in an analogous outcome.

In any of the examples listed above, pridopidine may be administered locally, i.e. by eye drops directly to the eye, and analogous results are obtained.

REFERENCES

"Glaucoma", Merck Manual of Diagnosis and Therapy (1999), Merck Research Laboratories, (Whitehouse Station, N.J.), 733-738.
Alward, "Medical Management of Glaucoma", N Eng J Med, 1998; 339:1298-1307).
Bakalash et al., "Resistance of Retinal Ganglion Cells to an Increase in Intraocular Pressure is Immune-dependent", Invest Ophthalmol Vis Sci 2002; 43:2648-2653.
Brod et al. (2000) Annals of Neurology, 47:127-131.
Cepurna et al. (2000) "Patterns of Intraocular Pressure Elevation After Aqueous Humor Outflow Obstruction in Rats." *Invest Ophthalmol Vis Sci.* 41(6) (May 2000):1380-5.
Coleman "Glaucoma", Lancet, 1999; 354:1803-1810.
CSID:25948790, www.chemspider.com/Chemical-Structure.25948790.html (accessed 23:27, Jul. 15, 2016).
CSID:7971505, www.chemspider.com/Chemical-Structure.7971505.html (accessed 23:33, Jul. 15, 2016).
Draize, J. H. (1965) "Appraisal of the Safety of Chemicals in Foods, Drugs, and Cosmetics." Association of Food and Drug Officials of the U.S., Austin, Tex., 1965. 36-45.
Farkas et al., "Apoptosis, Neuroprotection and Retinal Ganglion Cell Death: An Overview", Int Ophthalmol Clin 2001; 41:111-130.
Freireich et al. (1966) "Quantitative comparison to toxicity of anticancer agents in mouse, rat, hamster, dog, monkey and man." Cancer Chemother Rep, 50:219-244.
Guidance for Industry. In vivo drug metabolism/drug interaction studies—study design, data analysis, and recommendations for dosing and labeling, U.S. Dept. Health and Human Svcs., FDA, Ctr. for Drug Eval. and Res., Ctr. For Biologics Eval. and Res., Clin./Pharm., November 1999 www.fda.gov/cber/gdlns/metabol.pdf Hla et al. (2001) "Lysophospholipids—receptor revelations." 294(5548): 1875-8.

Horga and Montalban Jun. 4, 2008; Expert Rev Neurother., 2008; 8(5):699-714.

ISO/IEC 17025, 2005. General Requirements for the Competence of Testing and Calibration Laboratories.

Kipnis et al., "T Cell Immunity To Copolymer 1 Confers Neuroprotection On The Damaged Optic Nerve: Possible Therapy For Optic Neuropathies", Proc Natl Acad Sci 2000; 97:7446-7451.

Kleinschmidt-DeMasters et al. (2005) New England Journal of Medicine, 353:369-379.

Langer-Gould et al. (2005) New England Journal of Medicine, 353:369-379.

McDonald, and Shadduck (1983). Eye Irritation in Dermatotoxicology (2nd Ed.). Edited by Marzulli F. N. Hemishpere Publishing Corp., New York, N.Y.

Medeiros et al., "Medical Backgrounders: Glaucoma", Drugs of Today 2002; 38:563-570.

National MS Society Website, retrieved Jul. 10, 2012<www.nationalmssociety.org/ms-clinical-care-network/researchers/clinical-study-measures/index.aspx OECD 405, Organization for Economic Co-Operation and Development (OECD), Guidelines for the Testing of Chemicals, "Acute Eye Irritation/Corrosion", adopted 24 Apr. 2002.

Ollivier F. J., et al. (2007) "Ophthalmic Examination and Diagnostics Part 1: The Eye Examination and Diagnostic Procedure" in Veterinary Ophthalmology, 4th Ed. by Gelatt, K. N. 2007, 438-483. Blackwell Publishing, Gainesville, Fla.

PCT International Application Publication No. WO 2007/0047863, published Apr. 26, 2007.

PCT International Application Publication No. WO 2007/0146248, published Dec. 21, 2007.

Pezda; et al (2005) "Brn-3b Is Selectively Down-Regulated in a Mouse Model of Glaucoma". Investigative Ophthalmology & Visual Science 46:1327 abstract.

Polman et al. (2005) "Treatment with laquinimod reduces development of active MRI lesions in relapsing MS." Neurology. 64:987-991.

Polman et al. (2011) "Diagnostic Criteria for Multiple Sclerosis: 2010 Revisions to the McDonald Criteria." Ann Neural, 69:292-302.

Polman et al., (2005) "Diagnostic criteria for multiple sclerosis: 2005 revisions to the McDonald Criteria." Annals of Neurology, 58(6):840-846.

Rudick et al. (1999) "Use of the brain parenchymal fraction to measure whole brain atrophy in relapsing-remitting MS: Multiple Sclerosis Collaborative Research Group". Neurology. 53:1698-1704.

Runström et al. (2002) "Laquinimod (ABR-215062) a candidate drug for treatment of Multiple Sclerosis inhibits the development of experimental autoimmune encephalomyelitis in IFN-β knock-out mice," (Abstract), Medicon Valley Academy, Malmoe, Sweden.

Sandberg-Wollheim et al. (2005) "48-week open safety study with high-dose oral laquinimod in patients." Mult Scler. 11:S154 (Abstract).

U.S. Pat. No. 6,903,120, issued Jun. 7, 2005 (Sonesson, et al.)

U.S. Pat. No. 6,077,851, issued Jun. 20, 2000 (Bjork et al).

U.S. Pat. No. 7,589,208, issued Sep. 15, 2009 (Jansson et al).

U.S. Pat. No. 7,923,459, issued Apr. 12, 2011 (Gauthier, et al.)

PCT International Application Publication No. WO 2017/015609

Vollmer et al. (2008) "Glatiramer acetate after induction therapy with mitoxantrone in relapsing multiple sclerosis." Multiple Sclerosis, 00:1-8.

Weinreb et al., "Is Neuroprotection a Viable Therapy for Glaucoma?" Arch Ophthalmol 1999; 117:1540-1544.

Yang et al. (2004) "Laquinimod (ABR-215062) suppresses the development of experimental autoimmune encephalomyelitis, modulates the Th1/Th2 balance and induces the Th3 cytokine TGF-β in Lewis rats." J. Neuroimmunol. 156:3-9.

What is claimed is:

1. A method of treating a human subject afflicted with a neurodegenerative eye disease comprising administering to the subject an amount of pridopidine effective to treat the subject, wherein the pridopidine is administered via a systemic administration in an amount of pridopidine administered is 100 mg/day-315 mg/day, or via a local administration to the eye in an amount of 0.1 mg/day-50 mg/day.

2. The method of claim 1, wherein the administration of pridopidine is effective to reduce or inhibit a symptom of the neurodegenerative eye disease in the subject.

3. The method of claim 1, wherein the neurodegenerative eye disease is selected from the group consisting of glaucoma, Age-related Macular Degeneration, optic neuropathy, and retinitis pigmentosa.

4. The method of claim 3, wherein the neurodegenerative eye disease is Wet Age-related Macular Degeneration ("Wet AMD") or Dry Age-related Macular Degeneration ("Dry AMD").

5. The method of claim 3, wherein the neurodegenerative eye disease is Leber hereditary optic neuropathy.

6. The method of claim 3, wherein the neurodegenerative eye disease is glaucoma.

7. The method of claim 2, wherein the symptom is retinal ganglion cell damage or retinal ganglion cell loss.

8. The method of claim 1, wherein the amount of pridopidine is effective to reduce or prevent retinal ganglion cell loss or damage in the subject.

9. The method of claim 8, wherein the retinal ganglion cell loss is reduced by at least 10%, by at least 20%, by at least 30%, by at least 40% or by at least 50%.

10. The method of claim 8, wherein the retinal ganglion cell loss is reduced by more than 50%, more than 60%, more than 70%, or more than 80%.

11. The method of claim 1, wherein the amount of pridopidine is effective to improve retinal ganglion cell viability in a subject.

12. The method of claim 1, wherein the amount of pridopidine is effective to protect a retinal ganglion cell from cell death in the subject.

13. The method of claim 12, wherein the cell death is induced by elevated intraocular pressure.

14. The method of claim 1, wherein treating comprises slowing progression of the neurodegenerative disease of the eye in the subject.

15. The method of claim 1, wherein treating comprises slowing progression of visual field loss towards blindness in a subject afflicted with glaucoma.

16. The method of claim 1, wherein treating comprises preventing blindness in a subject afflicted with glaucoma.

17. The method of claim 1, wherein the treating comprises reducing axonal degeneration in the subject.

18. The method of claim 1, wherein pridopidine is pridopidine hydrochloride.

19. The method of claim 1, wherein the pridopidine is administered via a systemic administration.

20. The method of claim 19, wherein the pridopidine is administered in the form of an aerosol, an inhalable powder, an injectable, a liquid, a gel, a solid, a capsule or a tablet.

21. The method of claim 1, wherein the pridopidine is administered via a local administration to the eye.

22. The method of claim 21, wherein the pridopidine is administered in the form of a liquid, a gel, a cream or a contact lens.

23. The method of claim 21, wherein the pridopidine is administered in the form of eye drops, an intraocular depot injection, eye gels, a tablet inserted into the conjunctiva, or a lens loaded with pridopidine.

24. The method of claim 19 wherein the amount of pridopidine administered is 100 mg/day-250 mg/day or 100 mg/day-180 mg/day.

25. The method of claim 21, wherein the amount of pridopidine administered in a dose is 0.2 mg-20 mg.

26. The method of claim 1, wherein the pridopidine is administered periodically.

27. The method of claim 26, wherein pridopidine is administered daily.

28. The method of claim 26, wherein pridopidine is administered more often than once daily or less often than once daily.

29. The method of claim 26, wherein pridopidine is administered twice daily or thrice daily.

30. The method of claim 26, wherein pridopidine is administered every other day or weekly.

31. The method of claim 26, wherein the periodic administration of pridopidine continues for at least 3 days, more than 30 days, more than 42 days, 8 weeks or more, at least 12 weeks, at least 24 weeks, more than 24 weeks, 6 months or more, more than 12 months, more than 18 months, or more than 24 months.

32. The method of claim 1, wherein the subject is a human patient.

33. The method of claim 1, further comprising the administration of a second agent for the treatment of the neurodegenerative eye disease to the subject.

34. The method of claim 33, wherein the second agent is a β-adrenergic antagonist, adrenergic agonist, parasympathomimetic, agonist prostaglandin analog, or carbonic anhydrase inhibitor.

35. The method of claim 33, wherein the second agent reduces elevated intraocular pressure in a subject.

36. The method of claim 35, wherein the second agent is a prostaglandin agonist, a beta blocker, a carbonic anhydrase inhibitor, an alpha agonist, or a combination thereof.

37. The method of claim 35, wherein the second agent is latanoprost, bimatoprost, travoprost ophthalmic, unoprostone ophthalmic, tafluprost, Betaxolol ophthalmic, Carteolol, timolol, levobunolol, metipranolol, Dorzolamide, brinzolamide, acetazolamide, methazolamide, brimonidine, Apraclonidine, or a combination thereof.

38. The method of claim 33, wherein the subject is administered a fixed-dose combination comprising pridopidine and the second agent.

39. The method of 19, wherein the amount of pridopidine administered is 100 mg/day-180 mg/day.

40. The method of claim 19, wherein the pridopidine is administered via an oral administration.

41. The method of claim 21, wherein the pridopidine is administered via is a topical administration or via an intraocular, periocular, or ocular administration.

42. The method of claim 41, wherein the pridopidine is administered by an eye drop application to the conjunctiva.

* * * * *